(12) United States Patent
Yoshida et al.

(10) Patent No.: US 9,622,672 B2
(45) Date of Patent: Apr. 18, 2017

(54) DIGITALLY INVERTIBLE UNIVERSAL AMPLIFIER FOR RECORDING AND PROCESSING OF BIOELECTRIC SIGNALS

(71) Applicant: Indiana University Research and Technology Corporation, Indianapolis, IN (US)

(72) Inventors: Ken Yoshida, Carmel, IN (US); Kevin Mauser, Indianapolis, IN (US); Jan Stavnshoj, Aalborg (DK)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/896,337

(22) PCT Filed: Jun. 6, 2014

(86) PCT No.: PCT/US2014/041303
§ 371 (c)(1),
(2) Date: Dec. 4, 2015

(87) PCT Pub. No.: WO2014/197794
PCT Pub. Date: Dec. 11, 2014

(65) Prior Publication Data
US 2016/0120428 A1    May 5, 2016

Related U.S. Application Data

(60) Provisional application No. 61/832,469, filed on Jun. 7, 2013.

(51) Int. Cl.
*H03M 1/18* (2006.01)
*A61B 5/00* (2006.01)
(Continued)

(52) U.S. Cl.
CPC ...... *A61B 5/04004* (2013.01); *A61B 5/04001* (2013.01); *A61B 5/0402* (2013.01);
(Continued)

(58) Field of Classification Search
CPC ........ H03M 1/18–1/186; A61B 5/04–5/04004; A61B 5/0428; A61B 5/72–5/7296
(Continued)

(56) References Cited

U.S. PATENT DOCUMENTS 3,699,325 A * 10/1972 Montgomery, Jr. ... G01V 1/245
341/122
4,851,842 A * 7/1989 Iwamatsu ........... H03M 1/0639
330/144
(Continued)

OTHER PUBLICATIONS

International Search Report and Written Opinion issued by the Korean Intellectual Property Office, dated Sep. 29, 2014, for International Application No. PCT/US2014/041303; 9 pages.

*Primary Examiner* — Howard Williams
(74) *Attorney, Agent, or Firm* — Faegre Baker Daniels LLP

(57) ABSTRACT

A system for measuring electrical signals in a biological subject includes a variable gain amplifier with a predetermined transfer function that generates amplified signals corresponding to an input from electrical signals in the biological subject over a predetermined range of frequencies and amplification gain levels, an analog to digital converter generating digital data corresponding to the amplified signals, and a signal processing device receiving the digital data for the plurality of amplified signals. The signal processing device applies an inversion filter with another transfer function that is an inverse of the transfer function of the variable gain amplifier to remove an effect of the transfer function from the digital data, and generates an output signal
(Continued)

corresponding to the electrical signals in the subject with reference to the filtered digital data.

9 Claims, 7 Drawing Sheets

(51) Int. Cl.
    *A61B 5/04*     (2006.01)
    *A61B 5/0402*     (2006.01)
    *A61B 5/0476*     (2006.01)
    *A61B 5/0488*     (2006.01)

(52) U.S. Cl.
    CPC .......... *A61B 5/0476* (2013.01); *A61B 5/0488* (2013.01); *A61B 5/7203* (2013.01); *A61B 5/7225* (2013.01); *H03M 1/183* (2013.01)

(58) Field of Classification Search
    USPC .................................................. 341/139, 118
    See application file for complete search history.

(56) References Cited

U.S. PATENT DOCUMENTS

| | | | |
|---|---|---|---|
| 7,327,294 B2* | 2/2008 | Gierenz | H03M 1/0863 341/118 |
| 8,428,704 B2* | 4/2013 | Johnson | A61B 5/0006 600/517 |
| 9,294,121 B2* | 3/2016 | Qin | A61B 5/7217 |
| 2003/0097050 A1 | 5/2003 | Baru Fassio | |
| 2004/0092801 A1 | 5/2004 | Drakulic | |
| 2004/0106876 A1 | 6/2004 | Schmid et al. | |
| 2005/0215916 A1 | 9/2005 | Fadem et al. | |
| 2009/0093720 A1 | 4/2009 | Petersen et al. | |
| 2014/0025715 A1* | 1/2014 | Yang | G06F 17/10 708/131 |

\* cited by examiner

DIGITALLY INVERTIBLE UNIVERSAL AMPLIFIER FOR RECORDING AND PROCESSING OF BIOELECTRIC SIGNALS

CLAIM OF PRIORITY

This application is a U.S. National Phase filing of PCT/US14/41303, filed Jun. 6, 2014, which claims the benefit of U.S. Provisional Application No. 61/832,469, filed Jun. 7, 2013, the entire disclosures of both of which are hereby expressly incorporated by reference herein.

TECHNICAL FIELD

This disclosure is related to systems and methods for recording electrical activity in living subjects and, more particularly, to systems and methods for recording electrical signals that are generated during multiple types of nerve activity in a subject.

BACKGROUND

The recording and processing of bioelectric signals is an important monitoring technique for many scientific and medical procedures. Bioelectric signals refer to electrical signals that are generated in the bodies of living organisms in general, and to animals and humans in particular. Monitoring equipment records the electrical signals for display and analysis in automated systems or by scientists and medical professionals. Many existing systems that monitor electrical signals in a living subject perform amplification and filtering of the analog electrical signals that are measured in the subject prior to generating digital signal data using, for example, an analog to digital converter (ADC). Numerous data processing devices including personal computers (PCs) and specialized digital signal processor (DSP) devices perform additional processing of the digital signal data.

In a living organism, such as a human being, the ionic and chemical signaling mechanisms between cells in the body form the basis for the generation of bioelectric biopotentials. The biopotentials propagate and transmit information across electrically active tissues and between different locales in the body. The changes in biopotential occur due to the flow of different types of ions into and out of cells. In one example, the biopotential mechanisms include ionic gradients and voltage-gated sodium and potassium ion channels in different tissues in the body in order to convey information to different locations or tissues. The changes in biopotential occur at the cellular level when changes in trans-membrane potentials of a cell lead to the opening of sodium and potassium channels to permit ions into and out of the cell along electrochemical gradients.

The gradients occur because the concentration of sodium outside the cell is nearly 10 times higher, specifically 145 mM:15 mM ([out]:[in]), while the concentration of potassium inside the cell is nearly 27 times higher, specifically 120 mM:4.5 mM ([in]:[out]). The ionic concentration differential leads to a standing trans-membrane biopotential that can be momentarily discharged to transmit information from one part of the cell to another. The momentary discharge is manifested locally through the opening of voltage-gated ion-selective channels. As the channels open, the ions move down concentration gradients from regions of high concentration to low concentration. Thus, the sodium flows into the cell and potassium flows out of the cell. Specifically, once the trans-membrane potential is raised from −90 mV to about −70 mV due to a depolarizing stimulus, the sodium ion channels are activated and begin to let sodium ions into the cell. This migration causes the trans-membrane potential to become less negative and rapidly depolarizes the cell. As the cell depolarizes the potassium ion channels are activated and begin to release potassium ions into the interstitial space which slows the depolarization. As the depolarization slows down, the sodium ion channels close causing the depolarization to reverse since the potassium ion channels are still open and are releasing potassium ions. As the trans-membrane potential returns to −90 mV, the potassium ion channels gradually close causing the resting potential to be achieved. While at rest, the sodium-potassium pump actively restores the gradients for the next activation.

In different organisms, such as humans, the effects of the biopotentials in different types of nerve activity produce various types of electrical signals with different amplitudes, frequencies, and durations. Different types of bioelectrical signals are measured for different types of tissue and biological functions in the body. Common types of bioelectrical signals that are monitored in humans include electrocardiograms (ECG), electroencephalograms (EEG), electromyograms (EMG), and electroneurograms (ENG). The ECG signals originate in the heart. The ECG has frequency content that covers a wide range. The ECG includes three main waveforms: the P-wave, the QRS complex, and the T-wave. The P- and T-wave are comprised of lower frequency content in the tens of Hertz (Hz) while the QRS complex is a higher-frequency event that is centered near 150 Hz. Additionally, the amplitude of the QRS is approximately several millivolts (mV) and is larger than that of the P- or T-wave. The EEG signals originate in neurons inside the central nervous system. EEG signals generally contain low frequency information in a range of approximately 0.2 Hz to approximately 50 Hz and usually have amplitudes in the low microvolt range. The EMG signals originate in muscle fibers in the body. The EMG signals recorded during muscle contraction span a frequency range of 10 Hz to 2 kHz and vary in amplitude depending on their recording location but can range from a few microvolts to a few millivolts. The ENG signals originate from nerve axons in the peripheral nervous system. ENG signals usually have maximum amplitudes of several microvolts and the duration is approximately 1 ms but can vary widely. Its short duration seems to coincide with its high frequency content, which ranges from several hundreds of Hertz to tens of kilohertz.

During monitoring, another type of signal, the electrode-interface potential (EIP), is generated due to a voltage potential between one or more electrodes that are used to monitor bioelectric signals and the tissue in the subject around the electrodes. The EIP is not a bioelectric signal of interest for monitoring the subject, but is often present as a component in monitoring the other forms of bioelectric signals. In some monitoring conditions, the EIP signal has an amplitude that is larger than the amplitudes of the bioelectric signals that are generated in the subject.

The following table lists properties of the EIP, ECG, EEG, EMG, and ENG signals described above as observed in many human patients:

| Bioelectric Signal | Point of Origin | Frequency Bandwidth (Hz) | Amplitude | Duration |
| --- | --- | --- | --- | --- |
| Electrointerface Potential (EIP) | Tissue-Electrode Interface | 0-0.2 Hz | Low millivolts (mV) to volts (V) | Indeterminate (occurs during the entire monitoring period) |
| Electrocardiogram (ECG) | Heart | 0.2-200 Hz | 2-3 mV (QRS complex) | Up to 100 ms |
| Electroencephalogram (EEG) | Central Nervous system | 0.2-50 Hz | 10-300 μV | 5-10 ms |
| Electromyogram (EMG) | Muscles | 10 Hz-2 kHz | 5 μV-20 mV (surface); 50-1000 μV (invasive) | 2 ms |
| Electroneurogram (ENG) | Peripheral Nerves | 100 Hz-10 kHz | Low microvolts μV | 1 ms |

Drawbacks of present bioelectrical signal monitoring systems include the introduction of irreversible distortion to the electrical signals and the difficulty that present monitoring systems have with simultaneous monitoring of bioelectrical signals over a wide range of frequencies from direct-current (DC) to high-frequency signals. The distortion is introduced by the amplifiers and filters that are used to boost the bioelectrical signals and reduce noise, but the distortion can hinder analyses that rely on the unique morphological differences between bioelectric signal events. To generate amplified signals that minimize the distortion, existing monitoring systems are typically limited to monitoring a relatively narrow frequency range and are often only effective for monitoring the bioelectrical signals for a single type of nerve activity. The simultaneous monitoring of multiple types of nerve activity requires the use of multiple monitoring systems that are each configured to monitor different sets of bioelectrical signals in the subject. The limitations in current monitoring systems increase the difficulty in performing simultaneous monitoring of multiple types of electrical activity in a subject. Consequently, improved systems for measuring electrical signals corresponding to multiple types of nerve activity in a subject would be beneficial.

SUMMARY

An electrical monitoring system includes an invertible universal amplifier and digital restoration scheme. The universal amplifier is referred to as the invertible universal amplifier (IUA), while the universal amplifier and the digital restoration scheme together are referred to as the IUA system. As used herein, the "universal" amplifier is configured to provide varying amplification gain levels over different frequencies that correspond to multiple types of bioelectric signals in humans and other living subjects. The amplifier includes a transfer function that modifies the electrical signals and introduces some distortion to the relative amplitudes of signals at different frequencies. The system includes a digital processor that applies another transfer function that is the inverse of the transfer function of the amplifier to remove the distortion from digital data corresponding to the amplified signals. Thus, the system is "invertible" since the distortions introduced by the transfer function of the amplifier are removed from the digital data corresponding to amplified bioelectrical signals in the subject.

In one embodiment, a system for measuring electrical signals in a biological subject has been developed. The system includes a variable gain amplifier configured to generate a plurality of amplified signals corresponding to an input from a plurality of electrical signals measured in the biological subject over a predetermined range of frequencies at a plurality of predetermined amplification gain levels, the variable gain amplifier having a predetermined transfer function, an analog to digital converter (ADC) operatively connected to an output of the variable gain amplifier and configured to generate digital data corresponding to the plurality of amplified signals from the variable gain amplifier, and a signal processing device connected to an output of the ADC to receive the digital data corresponding to the plurality of amplified signals. The signal processing device is configured to apply an inversion filter to the digital data to generate filtered digital data, the inversion filter having another predetermined transfer function that is an inverse of the transfer function of the variable gain amplifier to remove an effect of the transfer function in the variable gain amplifier from the digital data, and generate an output signal corresponding to the plurality of electrical signals in the subject with reference to the filtered digital data.

DETAILED DESCRIPTION

Figure 1:
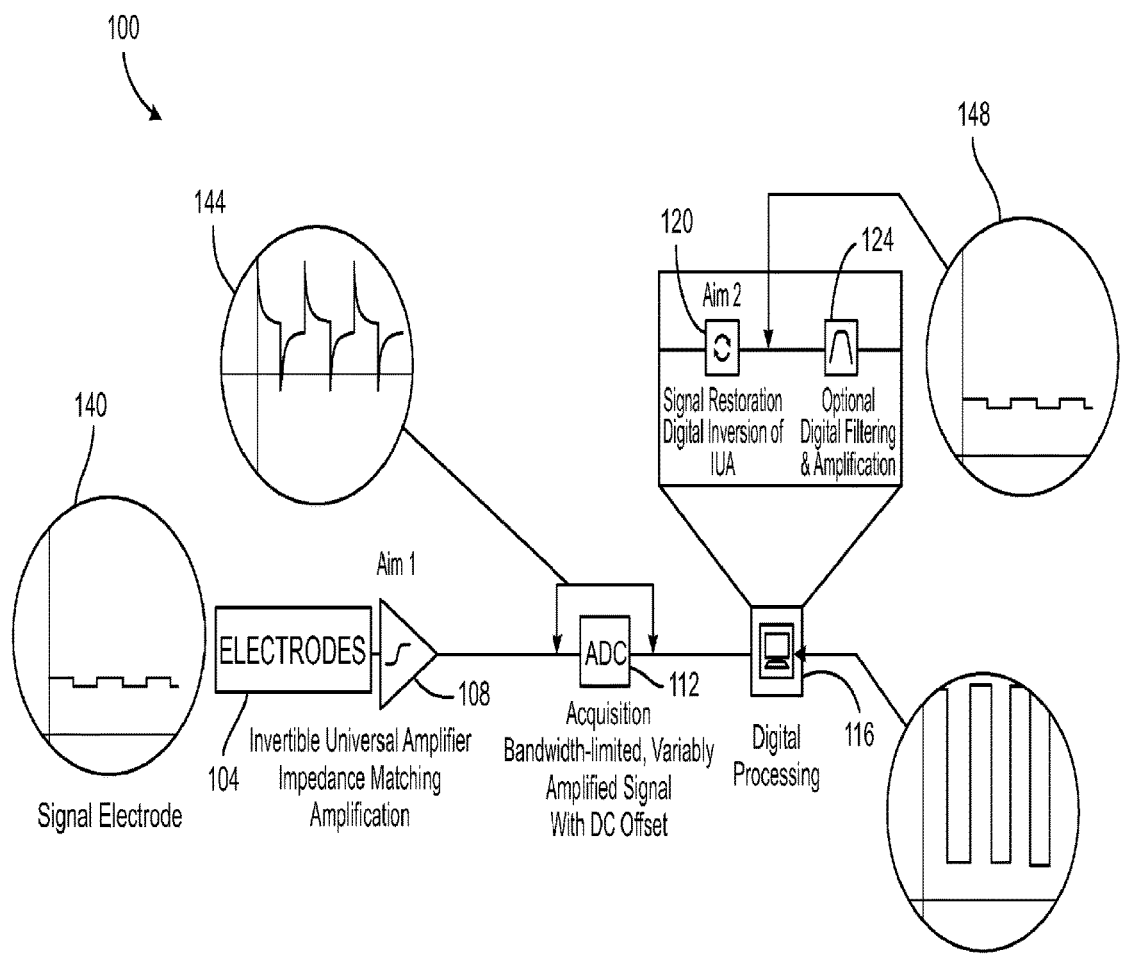
FIG. 1 is a schematic diagram of a system for monitoring multiple electrical signals in a living subject.

For a general understanding of the environment for the system and method disclosed herein as well as the details for the system and method, reference is made to the drawings. In the drawings, like reference numerals have been used throughout to designate like elements.

FIG. 1 depicts a monitoring system 100 for bioelectrical signals in a living subject. The system includes a plurality of electrodes 104 that receive electrical input signals from the subject, a variable gain amplifier 108 that amplifies the electrical input signals, an analog to digital converter (ADC) 112 that generates digital signal data corresponding to the amplified analog signals, and a digital processing device 116 that performs processing on digital signal data. The digital signal processing device 116 includes a signal restoration module 120 for removing distortions to the digital signal data that are introduced by the transfer function in the variable gain amplifier 108, and one or more digital filters and amplifiers 124 that perform additional modifications to the digital signal data. The digital processing device 116 includes a memory, such as a magnetic disk or solid-state storage device, which stores programmed instructions for performing processing of the digital signal data and optionally stores recordings of the digital signal data to record bioelectrical activity in the subject. In some embodiments, the digital processing device 116 includes an output device, such as a display monitor or plotting device, which produces a visual depiction of one or more electrical signals in the subject.

In the system 100, the electrodes 104 are placed on the skin of the subject or are implanted in the subject. In the system 100, the electrodes 104 are arranged in monopolar, unipolar, bipolar, tripolar or multipolar configurations that are known to the art. For monitoring the voltage of electrical signals in a subject, the electrodes 104 are configured to have high electrical impedance. An input to the amplifier 108 is also configured with a similar electrical impedance level in an impedance-matching configuration. The impedance matching reduces signal loss due to voltage division. Signal loss due to voltage division occurs when electrode interface impedance ($Z_e$) is relatively high, and approaches the input impedance ($R_i$) of the first stage amplifier. The potential at the input of the first stage amp becomes the ratio of $$\frac{R_i}{(R_i + |Z_e|)},$$

where $|Z_e|$ is the magnitude of $Z_e$. If $|Z_e| \sim R_i$, then there is a significant loss of potential. Impedance matching ensures that $R_i \gg |Z_e|$, which minimizes the potential loss.

Figure 2:
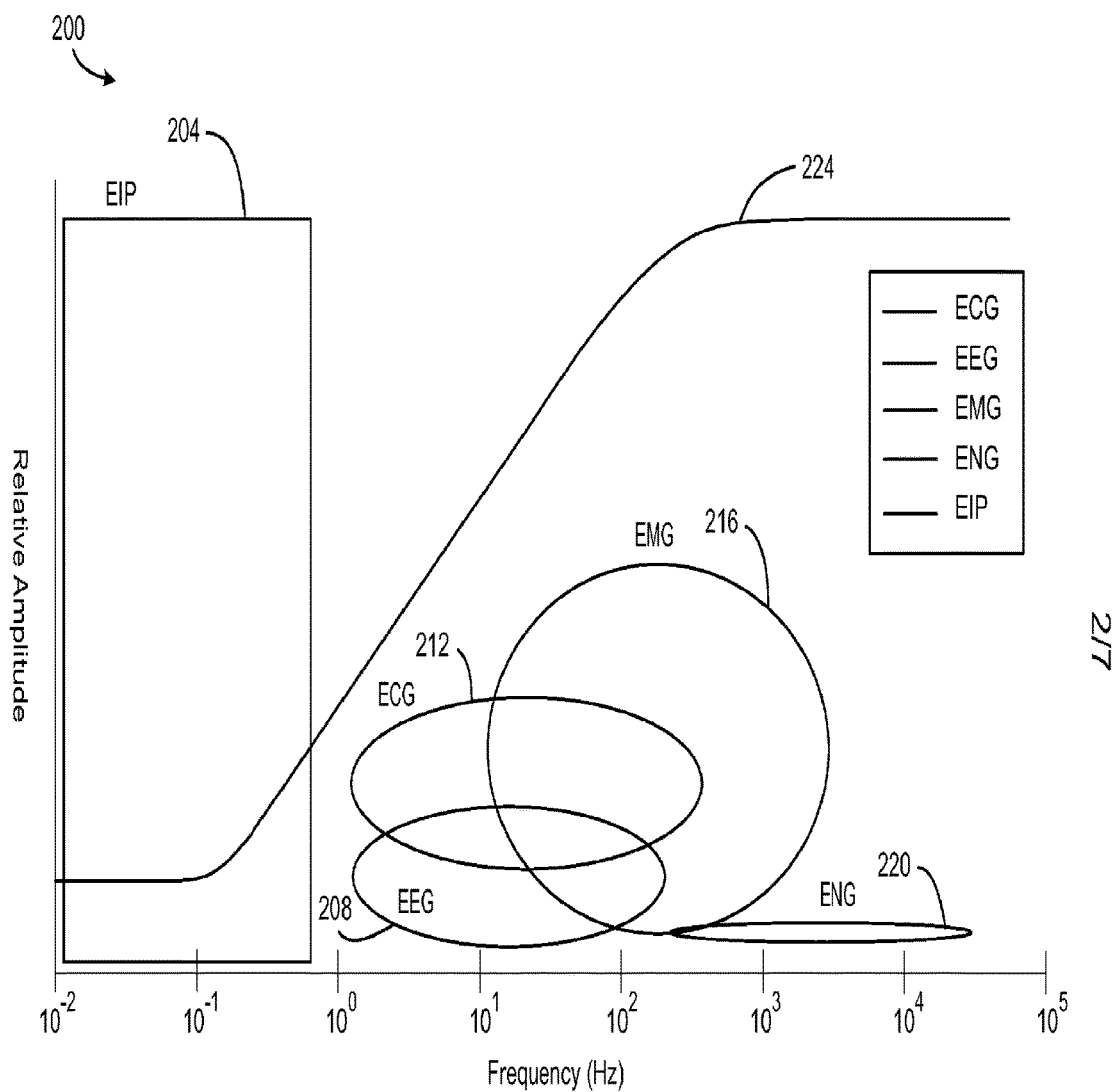
FIG. 2 is a graph depicting frequency and amplitude ranges for different types of bioelectrical signals in a subject and range of gain levels for a variable gain amplifier that amplifies the bioelectrical signals.

In the system 100, the variable gain amplifier 108 is configured to amplify electrical signals that are received from the electrodes 104. FIG. 2 depicts a graph 200 of the relative magnitudes and frequencies for the ECG, EEG, EMG, ENG, and EIP signals and a curve depicting the gain level of the amplifier 108 at different frequencies. In FIG. 2, the EIP signals 204 have the lowest frequency and highest overall amplitude. The bioelectrical ECG signals 208, EEG signals 212, EMG signals 216, and ENG signals 220 each include overlapping frequency and relative amplitude regions. While variations in the amplitudes and frequencies of the bioelectrical signals occur, a general trend depicted in FIG. 2 shows higher frequency signals having lower relative amplitudes than the lower frequency signals. In FIG. 2, the curve 224 depicts the gain level for the amplifier 108 at different frequencies. The amplifier 108 generates the lowest gain at low frequencies down to zero Hz (e.g. a DC voltage) and gradually increases to a maximum gain level at higher frequencies. In one embodiment, the amplifier 108 has a gain level of one (unity gain) in the lowest frequency range. The gain curve 224 is selected to generate amplified signals from the amplifier 108 that are below a saturation level for the amplifier given expected amplitudes of the detected bioelectric signals. For example, in one configuration the amplifier is configured to output amplified signals with a range of +/−9V, and any input signal that is amplified with a magnitude that exceeds the +/−9V range, then the amplifier 108 is saturated and outputs only the +/−9V signal instead of a waveform that approximates the input signal. Thus, the input signal is effectively truncated, which results in loss of information about the signal. The gain level is selected to minimize occurrences of saturations during the monitoring process.

Figure 3A:
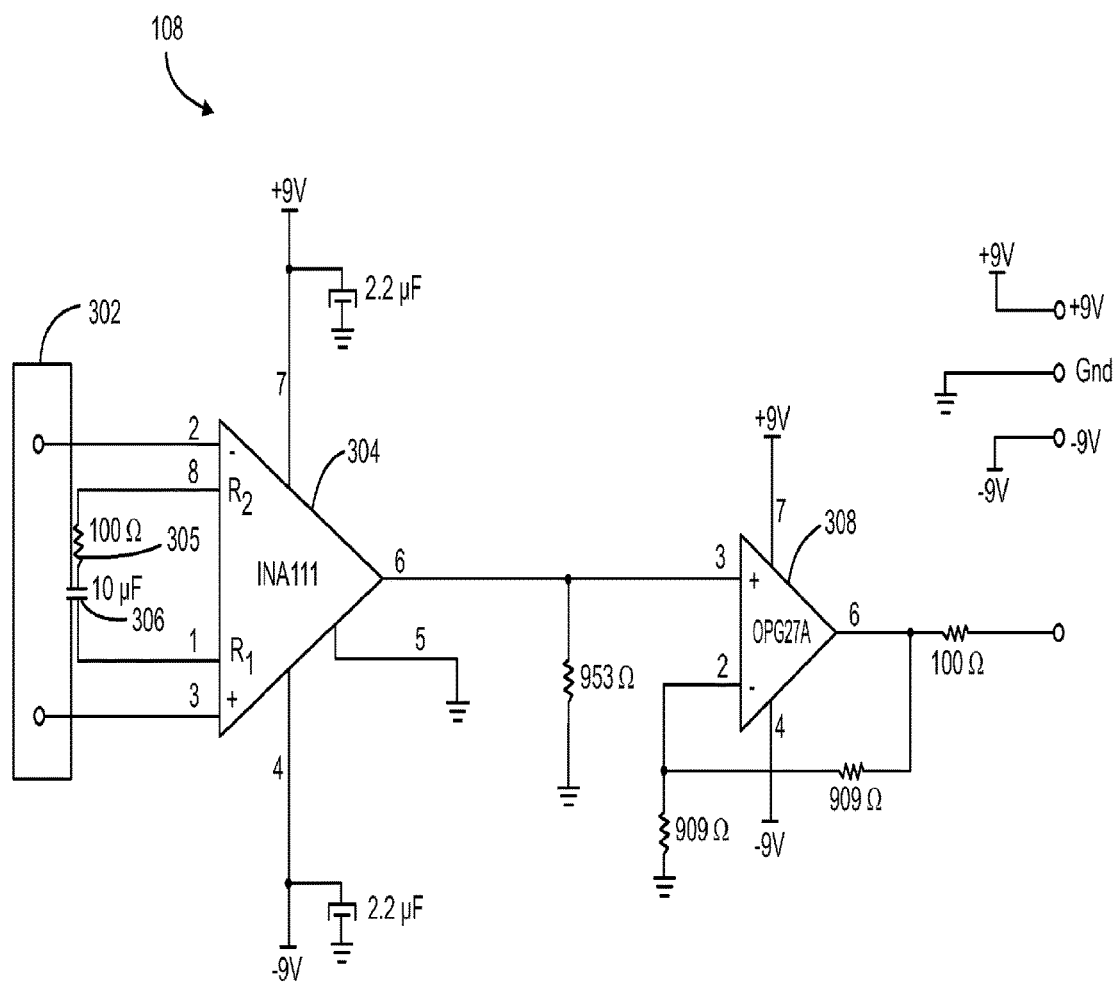
FIG. 3A is a schematic diagram of a variable gain amplifier with one variable-gain amplifier stage and a fixed-gain amplifier stage.

FIG. 3A depicts an embodiment of the variable gain amplifier 108 as a two-stage amplifier. In FIG. 3A, a first stage amplifier 304 receives the signals from the electrodes 104 through inputs 302. The first stage amplifier 304 is a high-impedance differential amplifier that is configured to match the impedance of the electrodes 104. A second stage amplifier 308 is configured in a fixed-gain mode to generate a fixed gain amplification of the output of the first stage amplifier 304. In the configuration of FIG. 3A, the second stage amplifier 308 is configured with a constant gain of two. In one embodiment, the first stage amplifier 304 is a Burr-Brown INA111AP high-speed FET input instrumentation amplifier that provides high input impedance, high common-mode rejection ratio (106 dB minimum), and high DC amplification accuracy. In a configuration for monitoring bioelectric signals in human subjects, the low-frequency corner of the amplifier 304 is set at 0.32 Hz and the high-frequency corner is set at 159 Hz forming a gain curve similar to the gain curve 224 depicted in FIG. 2, but with lower overall gain magnitude values. With a resistor and capacitor combination the instrumentation input stage incorporates the low-frequency corner set at 0.32 Hz with unity gain for lower frequencies, and the high-frequency corner set at 159 Hz with a gain of approximately 500. The second stage amplifier 308 includes a Texas Instruments OP27GP low-noise operational amplifier and was used for additional constant gain of two across all frequencies. Thus, the amplifier 108 is configured to generate a gain of two at frequencies below 0.32 Hz and a gain of 100 at frequencies above 159 Hz. The second stage amplifier multiplies the output of the first stage amplifier by the constant gain level to generate a variable frequency gain curve similar to the curve 224 depicted in FIG. 2.

Figure 4:
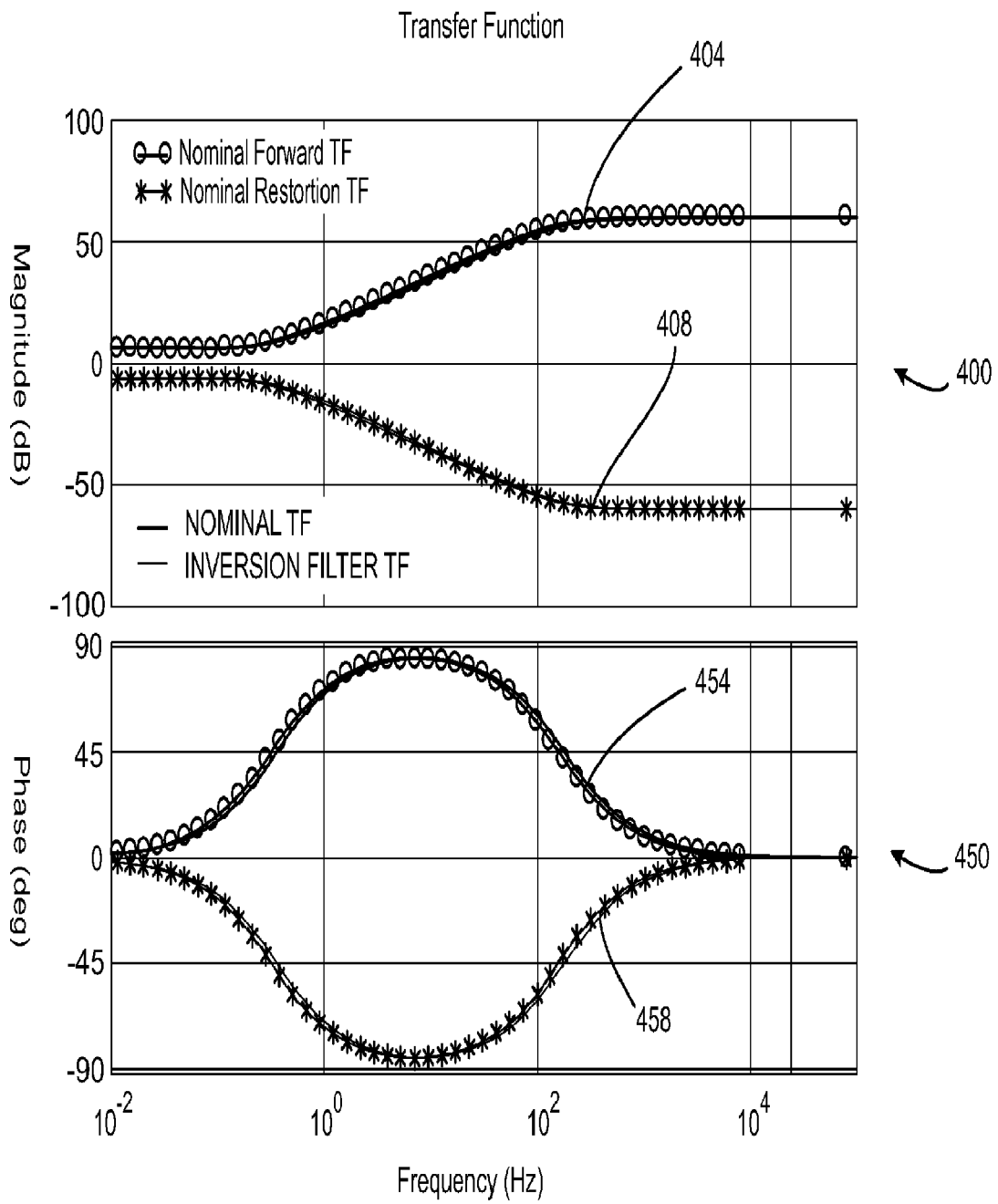
FIG. 4 is a set of graphs depicting magnitude and phase responses of a transfer function for a variable gain amplifier and an inverting transfer function for the system of FIG. 1.

The transfer function of the two-stage amplifier 108 over different frequencies ω is provided by the following equation:

$$TF = 2\left(\frac{j\omega C(R_1 + 2R_2) + 1}{j\omega CR_1 + 1}\right),$$

where resistor 305 is a 100Ω resistor $R_1$, C is the capacitance of capacitor 306 at 10 μF, and the resistor $R_2$ is a 25 KΩ resistor that is internal to the first stage amplifier 304. FIG. 4 depicts a bode diagram of the magnitude and phase of the transfer function for the amplifier 108. In the magnitude plot 400, the curve 404 depicts the gain of the amplifier 108 over a range of frequencies from 0 Hz (DC) to approximately 10 KHz. The phase plot 450 depicts a change in phase 454 that amplifier 108 introduces to the amplified signal. As depicted in FIG. 4, the phase curve 454 is non-zero for the majority of the frequency range, so the amplifier 108 changes both the magnitude and the phase of the input signal during the amplification process. In the configuration of FIG. 4, the amplifier is bounded-input bounded-output (BIBO) stable with a single pole at approximately −1005.25 in the left-hand portion of the complex plane. Additionally, the transfer function has a single zero with a value of approximately −1.885 in the open left-hand portion of the complex plane. As described below, an inversion filter uses the reciprocal of the transfer function for the variable gain amplifier 108, and the zero value in the open left hand plane becomes the pole of the inverted transfer function. Thus, both the transfer function for the amplifier 108 and the inverted transfer function are stable since both functions have poles that are located only in the open left hand portion of the complex plane.

Figure 3B:
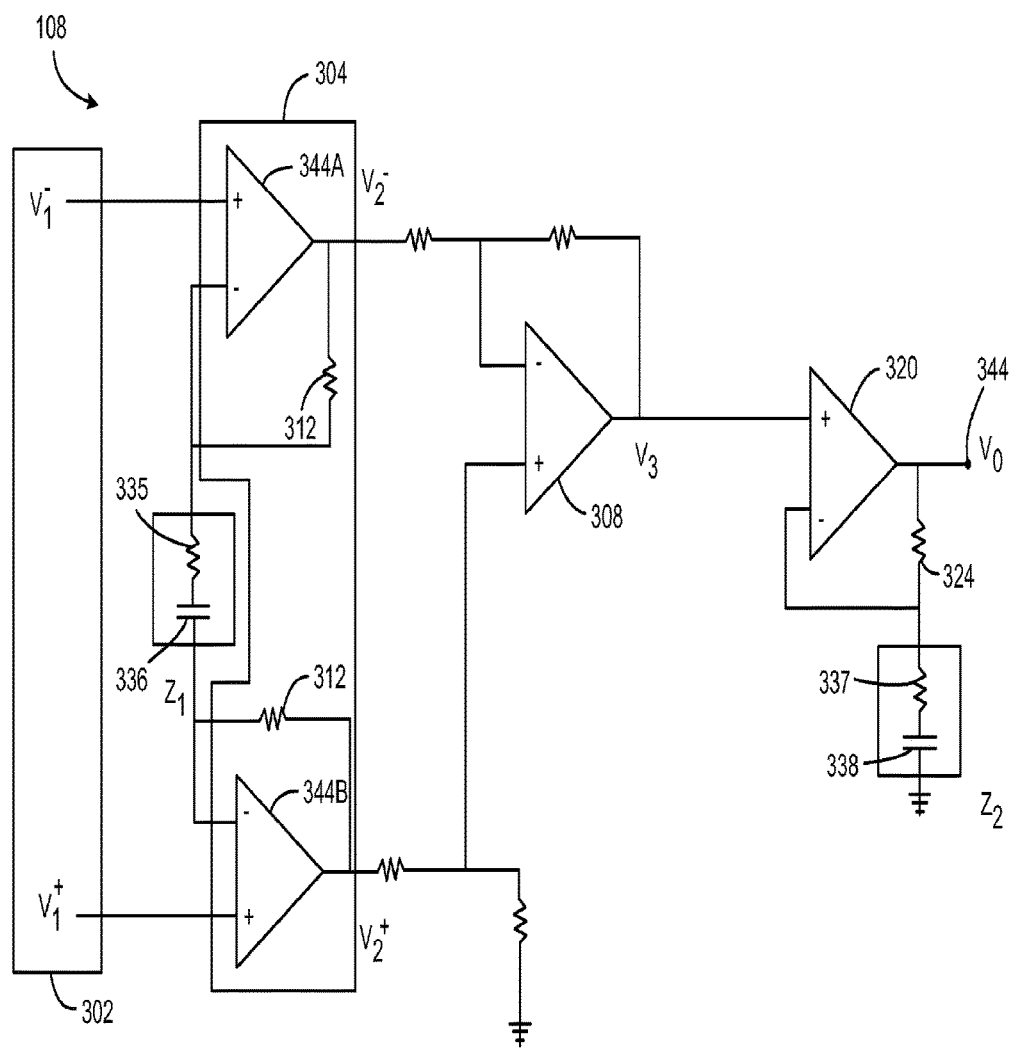
FIG. 3B is a schematic diagram of a variable gain amplifier with two variable-gain amplifier stages and a fixed-gain amplifier stage.

FIG. 3B depicts another embodiment of the amplifier 108 that includes three stages. In the embodiment of FIG. 3B, the amplifier 108 includes the first stage differential amplifier 304 that is embodied as two different operational amplifiers 344A and 344B that each have a positive input connected to one of the inputs $v_i^+$ and $v_i^-$. The resistors 312 depict feedback resistance for each of the operational amplifiers 344A and 344B. The negative terminals of the operational amplifiers 344A and 344B are connected to a series resistor 335 and capacitor 336 circuit. The circuit in the embodiment of FIG. 3B includes a smaller capacitor 336 than the capacitor 306 that is required in the amplifier of FIG. 3A due to the addition of a third stage variable gain amplifier 320 that includes another resistor 337 and capacitor 338.

The embodiment of FIG. 3B includes the fixed gain output amplifier 308 that generates a fixed gain output for input to a third stage operational amplifier 320. The third stage operational amplifier 320 includes a feedback loop with a resistor 324 and the resistor 324 is connected to another series circuit including a resistor 337 and capacitor 338, which includes another terminal that is connected to ground. The third stage amplifier 320 is another variable gain amplifier that generates an output voltage $v_O$ with a ratio of the output voltage $v_O$ at the output terminal 344 over the input voltage $v_3$ from the fixed gain amplifier 308 provided by the following equation:

$$\frac{v_O}{v_3} = \frac{R_4 + R_3 + (j\omega C_2)^{-1}}{R_3 + (j\omega C_2)^{-1}} = \frac{1 + (R_4 + R_3)j\omega C_2}{1 + j\omega R_3 C_2}.$$

The overall transfer function for the amplifier in FIG. 3B is provided by the following equation:

$$TF = \left(\frac{1 + j\omega C_1(R_1 + 2R_2)}{1 + j\omega C_1 R_1}\right)\left(\frac{1 + j\omega C_2(R_3 + R_4)}{1 + j\omega C_2 R_4}\right)$$

where $C_1$ is the first stage amplifier capacitor 336, $C_2$ is the third stage amplifier capacitor 338, $R_2$ is the resistance of each of the feedback resistors 312 in the first stage amplifier 304, $R_1$ is the resistor 335 that is connected to capacitor 336, $R_4$ is the feedback resistor 324 that is connected to the output of the amplifier 320, and $R_3$ is the resistor 337 that is connected to the capacitor 338. As the frequency approaches DC (0 Hz), the gain level in the transfer function approaches 1 (unity gain), at high frequencies, the gain level approaches:

$$\left(\frac{R_1 + 2R_2}{R_1}\right)\left(\frac{R_3 + R_4}{R_3}\right).$$

The additional stage in the amplifier 3B enables use of smaller capacitors 336 and 338 than in the two-stage embodiment of FIG. 3A (e.g. two 1 µF capacitors instead of a single 10 µF capacitor in some configurations of the amplifier in FIG. 3A). In integrated circuit embodiments of the amplifiers, the area taken up by the capacitors is a major component in the size of the integrated circuit, so the additional amplifier stage reduces the total size of the circuit. The multiple amplifier stages increase the gain at high frequencies to approximately 40 dB per decade to enable the amplifier to operate with a gain of near unity at low frequencies and a high gain at higher frequencies. Use of a large capacitor in the embodiment of FIG. 3A is necessary due to the lower 20 dB per decade $1^{st}$ order response of the system to obtain a sufficient gain at high frequencies in the neural frequency band. Alternative embodiments that include additional amplifier stages added can incorporate even smaller capacitors with tradeoffs in reduced amplifier stability, inverting digital filter stability, and the added requirement of tighter tolerances for the values of the components used and their characterization.

Referring again to FIG. 1, the ADC 112 receives the output of the variable gain amplifier 108. The ADC 112 generates digital data corresponding to the analog data at a predetermined sampling rate with a predetermined number of quantization states for each sample. For example, in one embodiment the ADC is a twelve-bit ADC with $2^{12}$ (4096) digital quantization levels between input voltage levels of +/−10V, and the ADC generates samples at a rate of 48 KHz. As is known in the art, converting the amplified analog signal to a digital representation introduces some degree of error since the digital data cannot represent every possible value of the analog signal at all times and amplitudes. The amplified signal, however, expands the original biometric signals over a much larger range to enable the ADC 112 to generate digital data using a greater proportion of the range for the ADC 112 than would occur if the original bioelectrical signals are provided to the ADC 112 directly. The amplified signals also include amplified portions of electrical noise in the subject including the EIP signal. As described above, however, the variable gain amplifier 108 is configured with higher gain levels in the frequency ranges for the bioelectric signals to increase the relative signal to noise ratio for the bioelectric signals in the amplified signal.

In the system 100, the digital processing device 116 receives digital data from the ADC 112 corresponding to the amplified signal. The digital processing device 116 is, for example, a personal computer (PC) with a central processing unit (CPU), graphical processing unit (GPU), digital signal processors (DSPs), or any other combination of digital processing hardware and software that are configured to extract data corresponding to the original bioelectric signals from the digital signal data. For example, the variable gain amplifier 108 transforms the original time valued bioelectric signals x(t) into a series of amplified signals y(t) via convolution according to the following time-domain transform equation: y(t)=kh(t)*x(t) where h(t) corresponds to the transformation of the original signal x(t) and k is a constant. Such transformations are commonly expressed in the frequency domain using, for example, the Laplace transform to identify the transformation in the frequency domain according to the following equations:

$$X(s) = \int_0^\infty x(t)e^{-st}dt$$

$$Y(s) = kH(s)X(s)$$

In the equation above, H(s) corresponds to a continuous-time transfer function of the variable gain amplifier 108. Since the digital processing device 116 receives discrete time digital signal data, the equations above are expressed using the discrete time z-transformation:

$$X(z) = \Sigma_{n=0}^\infty x[n]z^{-n}$$

$$Y(z) = kH(z)X(z)$$

As described above, the digital processing device 116 includes the restoration module 120 that is configured to remove the effects of the transfer function in the variable gain amplifier from the digital signal data represented by Y(z). The restoration module 120 includes an inversion filter that is the inverse of the transfer function in the amplifier 108. As used herein, the term "inversion filter" refers to any operation performed on a signal by digital processing hardware and software or other signal processing devices that removes the effects of a transfer function that has been applied to the signal by another device, such as the amplifier 108 in the example of FIG. 1. Mathematically, the inversion filter function C(s) is expressed as the inverse of the transfer function H(s) of the variable gain amplifier 108:

$$C(s) = \frac{1}{kH(s)}.$$

Thus, given the transformed signal Y(s), the inversion filter enables reconstruction of the original signal X(s) through multiplication: X(s)=Y(s)C(s). In the discrete signal domain of digital data, the reconstruction equation is: X(z)=Y(z)C(z).

In the system 100, the digital processing device 116 implements the inversion filter C(s) using software and hardware digital processing modules that apply the inverse of the identified transfer function of the variable gain amplifier 108 to the digital data received from the ADC 112. For the transfer function TF provided above for the embodiments of the variable gain amplifier 108 in FIG. 3A and FIG. 3B, the inversion filter transfer function corresponds to $TF^{-1}$, as set forth in the following equation:

$$TF^{-1} = \frac{1}{2}\left(\frac{j\omega CR_1 + 1}{j\omega C(R_1 + 2R_2) + 1}\right).$$

FIG. 4 depicts graphs of the inverse transfer function including a magnitude graph 408 and phase graph 458. As depicted in FIG. 4, the combination of the original transfer function and the inverse transfer function in the inversion filter cancels the transformation of the original signal and returns the original value of the input signal over a wide range of frequencies. For example, combining the magnitude transfer function curves 404 and 408 over a range of frequencies yields a magnitude change of 0 dB, which is effectively the magnitude of the original signal over the frequency range. Similarly, combining the phase graphs 454 and 458 over the range of frequencies results in a phase change of zero.

During operation, the system 100 records bioelectric signals from a subject using the electrodes 104, amplifies the signals with the variable gain amplifier 108, generates digital data from the signals using the ADC 112, and then performs additional processing with the digital processing device 116 to apply the inverted transfer function to the digital data using the signal restoration module 120. The digital processing device 116 optionally applies one or more filters or amplifiers 124 to the digital signal data after the application of the inverted transfer function.

In the example of FIG. 1, the electrodes 104 detect an illustrative square wave signal 140. The variable gain amplifier 108 generates an amplified analog signal 144 from the input signal 140. The transfer function of the variable gain amplifier 108 generates peak distortions in the amplified signal 144. The ADC 112 receives the amplified analog signal 144 and generates a digital representation of the amplified signal. Because the signal 144 is amplified, the digital data from the ADC 112 use a larger portion of the dynamic range of the ADC 112 than would be used if the original signal 140 were to be supplied to the ADC 112 directly. The digital signal data include the distortions that are introduced by the amplifier 108, however. The digital processing device 116 applies the predetermined inverted transfer function using the signal restoration module 120, and the inverted transfer function removes the effects of the amplifier 108, including both the amplification and distortion of the analog signal, are removed from the original signal to generate the digital signal 148. The digital signal 148 that corresponds to the original analog signal 140, with the signal distortion errors that are introduced by the amplifier 108 minimized in the output signal. Thus, the amplifier 108 provides variable gain amplification to different bioelectric signals over a wide frequency range to enable the ADC 112 to generate digital representations of the amplified analog signals with high resolution to provide a digital signal with high precision. The digital processing device 116 and signal restoration module 120 then apply the inverse transfer function to the digital data to remove the inherent distortions from the amplifier 108 to generate the final digital output signal with high precision and high accuracy.

In the system 100, the restoration module 120 applies the inversion filter to the digital data from the ADC 112 to generate a digital representation of the original bioelectrical signals that are received from the subject through the electrodes 104. In an ideal system, the transfer function for the variable gain amplifier 108 and corresponding inverted transfer function used in the inversion filter are accurately defined using the nominal capacitance and resistance values for the variable gain amplifier 108. In a practical embodiment of the system 100, however, the parameters that define the transfer function for the variable gain amplifier 108 vary from the nominal parameters. For example, components in individual amplifier circuits have varying characteristics due to the tolerances of materials and components that are used to manufacture the amplifier. Additionally, the characteristics of different components in the system 100 can vary during operation due to, for example, changes in the operating temperature amplifier and changes to component characteristics due to age.

Inaccuracies in the characterization of the transfer function for the variable gain amplifier 108 produce corresponding inaccuracies in the output of the inversion filter in the signal restoration module 120. Furthermore, the errors in characterizing the inverse transfer function $TF^{-1}$ in the inversion filter can affect the location of the poles for the inverse transfer function. As described above, the inverse transfer function $TF^{-1}$ has poles that are in the open left hand complex plane if the inverse transfer function accurately reflects the transfer function TF of the variable gain amplifier 108. However, comparatively small errors in the identified transfer function for the variable gain amplifier 108 may generate shifts in the effective locations for the poles from the left hand complex plane to introduce instability in the inversion filter.

Figure 5:
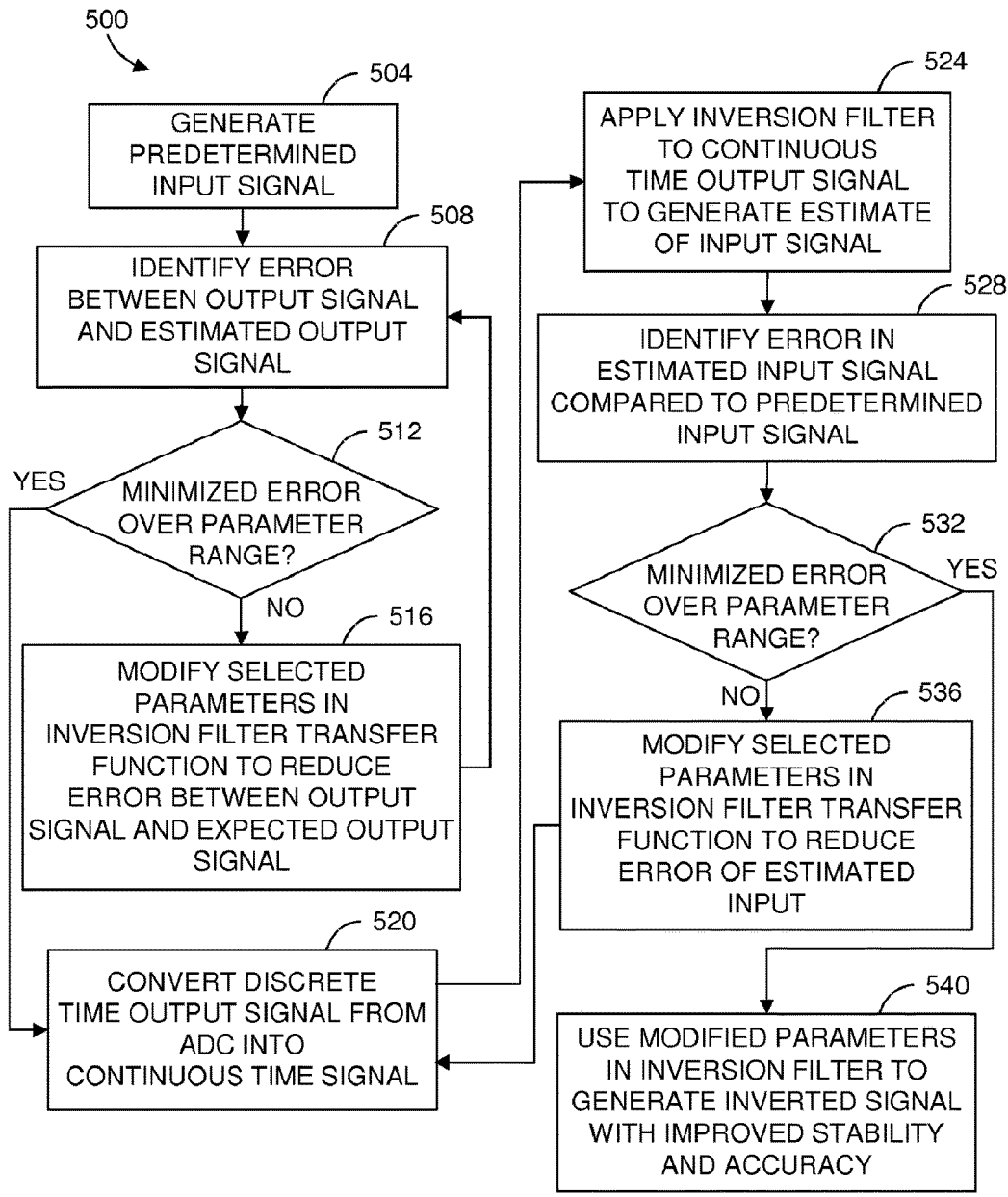
FIG. 5 is a block diagram of a process for characterizing a transfer function of a variable gain amplifier in the system of FIG. 1 and for adjusting an inverse transfer function of an inversion filter in the system of FIG. 1 to reduce error in generating a reconstruction of an input signal in the system of FIG. 1.

FIG. 5 depicts a process 500 for modifying one or more parameters in the inverse transfer function for the inversion filter to improve the accuracy of the characterization of the variable gain amplifier. In the discussion below, a reference to the process 500 performing an action or a function refers to the operation of a digital processor or controller, such as the digital processing device 116, executing stored program instructions to perform the action or function. The process 500 is described in conjunction with the system 100 of FIG. 1 for illustrative purposes.

Process 500 begins with generation of a predetermined input signal for the system 100 (block 504). In one configuration, a signal generator produces a square wave with a frequency of 1 Hz as the predetermined signal. Another configuration uses multiple predetermined input signals during the process 500 including square waves, sinusoidal waves, and triangle waves at frequencies of between 1 Hz up to several kilohertz with amplitudes between −2 V and 2V. An external signal generator produces the predetermined signals and signals are applied to the input of the variable gain amplifier 108 through the electrodes 104 or through another electrical connection.

Process 500 continues with an output error (OE) estimation process that modifies one or more selected parameters in the transfer function of the variable gain amplifier 108 to reduce identified errors in the output signal from the amplifier 108 to below a predetermined error threshold. During process 500, a signal acquisition device measures the analog output signal from the variable gain amplifier 108. Since the input signal that is supplied to the amplifier 108 is a predetermined signal, the estimated output of the amplifier is another predetermined amplified signal. The digital signal processing device 116 or another signal processing device identifies an error between the measured output of the amplifier 108 and the expected output (block 508). The estimated output is identified using the transfer function TF for the variable gain amplifier 108 applied to the predetermined input signal. In one embodiment, the transfer function TF is initialized with the nominal resistor and capacitor values $R_1$, $R_2$, and C for the amplifier 108.

If the identified error between the measured and estimated outputs for the amplifier 108 is not a minimum error over a predetermined range of parameter values (block 512), the digital processing device 116 modifies one or more of the parameters for the transfer function TF to reduce the error between the measured and estimated outputs from the amplifier 108 (block 516). The digital processing device 116 changes at least one of the parameters in the transfer function TF that corresponds to a component in the amplifier 108, such as the parameters $R_1$, $R_2$, and C. In one embodiment, the process 500 adjusts the value for one of the parameters while the remaining parameters remain constant. During process 500, the output-error estimation described above with reference to the blocks 508-516 continues in an iterative manner over a predetermined range of parameter values for the transfer function TF until the minimum error between the measured output of the amplifier 108 and the estimated output signal generated using the transfer function TF is identified.

In some embodiments of the process 500, the output-error estimation process modifies the parameters of the transfer function TF, and the modified parameters are then used in the inverse transfer function $TF^{-1}$ in the restoration module 120. While the output-error estimation process can reduce the error between the parameters used in the transfer function and inverse transfer function, the purpose of the restoration module 120 is to generate a reconstruction of the original input signal to the variable gain amplifier 108 instead of the output of the variable gain amplifier 108. The output-error estimation process does not necessarily generate transform function parameters that minimize the input error. Consequently, in the embodiment of FIG. 5, the process 500 uses the results of the output-error estimation process as an initial estimates for the parameters in the transfer function for the amplifier 108, and continues using an input-error estimation process to modify the parameters and further reduce the errors between the input signals and the reconstructed input signals that are generated by the restoration module 120.

In the process 500, the input-error estimation process begins with conversion of the discrete time output signal from the ADC 112 into a continuous time signal (block 520). The input-error process begins with the digitized signal from the ADC 112 because the digitized, discrete time output of the ADC 112 is received by the inversion filter in the restoration module 120. The discrete time signal, however, lacks sufficient excitability for direct use in identifying an error between the estimated input signal from the inverse transfer function $TF^{-1}$ and the predetermined input signal that is supplied to the amplifier 108. In one embodiment, a software analysis tool such as Matlab or another appropriate software program generates the continuous time representation of the signal. Additionally, the input-error estimation process uses the continuous time domain representation of the inverse transfer function $$\left(\frac{1}{kH(s)}\right)$$

instead of the discrete time domain representation $$\left(\frac{1}{kH(z)}\right),$$

although the resistance and capacitance parameters are applicable to both the discrete time and continuous time domain inverse transfer functions.

Process 500 continues with generation of an estimate of the original input signal using the continuous-time input signal data and the continuous-time inverse transformation $TF^{-1}$ (block 524). In the system 100, the digital signal processing device 116 applies the inversion filter to the continuous time representation of the signal and identifies an error between the estimated input signal from the inversion filter and the predetermined input signal from the signal generator (block 528). If the identified error is not a minimized error over a predetermined range of parameter values (block 532), then the digital signal processing device 116 modifies one or more of the parameters for the inverse transformation $TF^{-1}$, such one or more of the parameters $R_1$, $R_2$, and C (block 536). The input-error estimation processing described above in blocks 520-536 continues in an iterative manner until the inverse transformation function $TF^{-1}$ with the modified parameters generates an estimate for the input signal with a minimum error for a predetermined range of inverse transfer function parameter values (block 532). During the iterative process, the selected parameters are either increased or decreased to modify the estimated input signal. In one embodiment, the digital processing device 116 increments or decrements the parameter values by a predetermined amount over a range of parameter values until identifying parameters that generate the estimated input signal with the minimum error.

Figure 6:
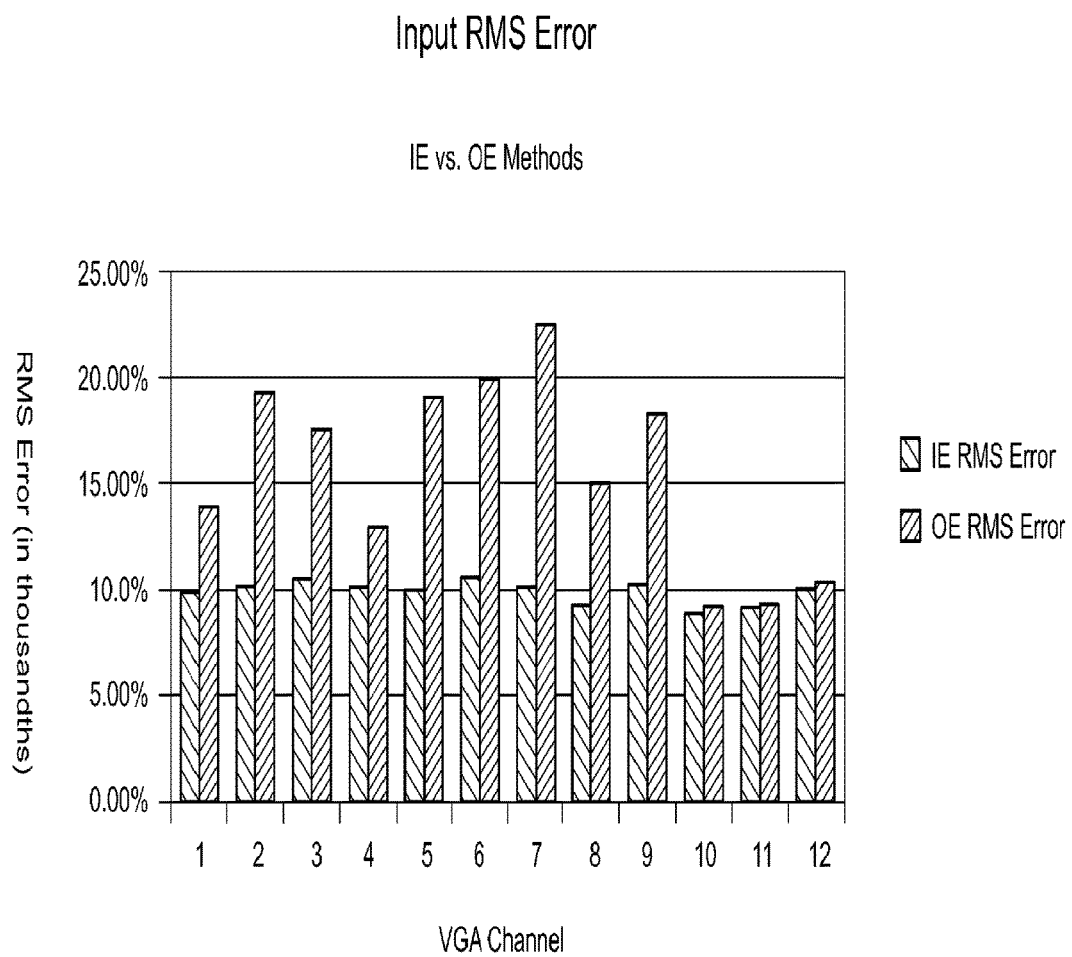
FIG. 6 is a chart depicting error between an input signal and an output signal from the inversion filter of FIG. 1 using the process of FIG. 5.

After identification of the parameters for the input-error estimation process, the digital processing device 116 stores the modified parameters for the inversion filter in a memory for use in generating inverted signals with improved accuracy and stability (block 540). In one configuration, the process 500 is performed during manufacture of the system 100 to characterize the variable gain amplifier 108 in operation with the system 100. In another configuration, the process 500 is performed periodically prior to using the system 100 to monitor bioelectrical signals in a subject. The process 500 can be performed multiple times at different operating temperatures for the system 100 to identify the parameters for the inverse transfer function $TF^{-1}$ over a range of operating temperatures. FIG. 6 depicts illustrative root-mean-square (RMS) errors that are achieved for multiple channels of a bioelectric monitoring system using both the output-error (OE) estimation process and the input-error (IE) estimation process in conjunction with the OE process. As depicted in FIG. 6, the IE estimation process enables modification of the parameters in the inverse transfer function $TF^{-1}$ to reduce the error between the original input signal from the subject and the reconstructed input signal from the restoration module 120 beyond the minimum error levels for the OE method.

While the embodiments have been illustrated and described in detail in the drawings and foregoing description, the same should be considered as illustrative and not restrictive in character. Additional details related to the embodiments described herein are included in the attached appendix, the contents of which are expressly incorporated herein. It is understood that only the preferred embodiments have been presented and that all changes, modifications and further applications that come within the spirit of the invention are desired to be protected as set forth in the following claims.

The invention claimed is:

1. A system for measuring electrical signals in a biological subject comprising:
a variable gain amplifier configured to generate a plurality of amplified signals corresponding to an input from a plurality of electrical signals measured in the biological subject over a predetermined range of frequencies at a plurality of predetermined amplification gain levels, the variable gain amplifier having a predetermined transfer function;
an analog to digital converter (ADC) operatively connected to an output of the variable gain amplifier and configured to generate digital data corresponding to the plurality of amplified signals from the variable gain amplifier;
a signal processing device connected to an output of the ADC to receive the digital data corresponding to the plurality of amplified signals, the signal processing device being configured to:
apply an inversion filter to the digital data to generate filtered digital data, the inversion filter having another predetermined transfer function that is an inverse of the transfer function of the variable gain amplifier to remove an effect of the transfer function in the variable gain amplifier from the digital data; and
generate an output signal corresponding to the plurality of electrical signals in the subject with reference to the filtered digital data;
a signal generator configured to generate a predetermined signal for input to the variable gain amplifier;
a signal acquisition device configured to measure another signal from the output of the variable gain amplifier corresponding to the amplified predetermined signal; and
the signal processing device being connected to the signal acquisition device and further configured to:
identify an error between the signal from the variable gain amplifier corresponding to the amplified predetermined signal and an expected amplified signal corresponding to the predetermined input signal, the expected amplified signal being identified with reference to the predetermined transfer function of the amplifier;
modify a parameter in the predetermined transfer function of the variable gain amplifier to reduce or eliminate the identified error; and
store the modified parameter in a memory for use in the predetermined transfer function of the inversion filter to reduce an error in the output signal.

2. The system of claim 1, the variable gain amplifier being configured to amplify each of the plurality of signals at each of the plurality of frequencies by an amount that generates the amplified signals with less than a predetermined direct current (DC) saturation level for the variable gain amplifier.

3. The system of claim 1, the variable gain amplifier further comprising:
a high-impedance first stage operational amplifier that is configured to receive the plurality of electrical signals measured in the living subject.

4. The system of claim 3, the variable gain amplifier further comprising:
a low-noise constant gain second stage operational amplifier configured to generate an output with a constant gain from an input signal received from the first stage operational amplifier.

5. The system of claim 4, the variable gain amplifier further comprising:
a variable gain third stage operational amplifier configured to generate another output with reference to the output from the second stage operational amplifier.

6. The system of claim 1 wherein the transfer function of the variable gain amplifier changes an amplitude and a phase of at least one of the plurality of electrical signals.

7. The system of claim 6 wherein the inverse filter removes the change in amplitude and phase from the transfer function of the variable gain amplifier for the digital data corresponding to the at least one electrical signal.

8. The system of claim 1 wherein the variable gain amplifier is configured to amplify a signal at a first frequency with a first gain level and a signal at a second frequency with a second gain level, the first frequency being lower than the second frequency and the first gain level being lower than the second gain level.

9. The system of claim 1, the signal processing device being further configured to:

generate data corresponding to a continuous time domain representation of the digital data from the ADC;
generate a continuous time filtered signal from the data corresponding to a continuous time representation of the digital data from the ADC using a continuous time representation of the inversion filter;
identify another error between the predetermined input signal and the continuous time filtered signal;
modify the parameter in the predetermined transfer function of the inversion filter to reduce or eliminate the other identified error; and
store the modified parameter in the memory for use in the predetermined transfer function of the inversion filter to reduce an error in the output signal.

* * * * *